US006294172B1

(12) United States Patent
Bosslet et al.

(10) Patent No.: US 6,294,172 B1
(45) Date of Patent: Sep. 25, 2001

(54) MONOCLONAL ANTIBODIES WITH SPECIFICITY FOR MEMBRANE-ASSOCIATED ANTIGENS

(75) Inventors: Klaus Bosslet; Roland Kurrle; Hans Harald Sedlacek, all of Marburg; Ernst-Jurgen Kanzy, Weimar-Niederweimar; Takako Katoh, Marburg; Hans Ulrich Schorlemmer, Marburg; Gerhard Luben, Marburg, all of (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/383,678

(22) Filed: Feb. 1, 1995

Related U.S. Application Data

(63) Continuation of application No. 08/134,869, filed on Oct. 12, 1993, now abandoned, which is a continuation of application No. 07/967,563, filed on Oct. 28, 1992, now abandoned, which is a continuation of application No. 07/544,651, filed on Jun. 27, 1990, now abandoned, which is a continuation-in-part of application No. 07/425,449, filed on Oct. 23, 1989, now abandoned, which is a continuation of application No. 07/223,773, filed on Jul. 25, 1988, now abandoned, which is a continuation of application No. 07/080,248, filed on Jul. 27, 1987, now abandoned, which is a continuation of application No. 06/639,310, filed on Aug. 10, 1984, now abandoned, application No. 08/383,678, which is a continuation-in-part of application No. 07/418,722, filed on Oct. 3, 1989, now abandoned, which is a continuation of application No. 07/246,011, filed on Sep. 14, 1988, now abandoned, which is a continuation of application No. 06/729,578, filed on May 2, 1985, now abandoned, application No. 08/383,678, which is a continuation-in-part of application No. 07/523,835, filed on May 1, 1990, now abandoned, which is a continuation of application No. 07/387,444, filed on Jul. 31, 1989, now abandoned, which is a continuation of application No. 07/261,925, filed on Oct. 25, 1988, now abandoned, which is a continuation of application No. 07/129,896, filed on Nov. 24, 1987, now abandoned, which is a continuation of application No. 06/772,446, filed on Sep. 4, 1985, now abandoned, application No. 08/383,678, which is a continuation-in-part of application No. 07/565,166, filed on Aug. 10, 1990, now abandoned, which is a continuation of application No. 07/223,734, filed on Jul. 22, 1988, now abandoned, which is a continuation of application No. 06/901,873, filed on Aug. 29, 1986, now abandoned, application No. 08/383,678, which is a continuation-in-part of application No. 07/456,199, filed on Dec. 20, 1989, now abandoned, which is a continuation of application No. 07/203,637, filed on Jun. 3, 1988, now abandoned, which is a continuation of application No. 07/090,604, filed on Aug. 28, 1997, now abandoned.

(30) Foreign Application Priority Data

| Aug. 12, 1983 | (DE) | 33 29 184 |
| May 7, 1984 | (DE) | 34 16 774 |
| Sep. 6, 1984 | (DE) | 34 32 714 |
| Sep. 2, 1985 | (DE) | 35 31 301 |
| Aug. 30, 1986 | (DE) | 36 29 640 |

(51) Int. Cl.⁷ ..................... A61K 39/395; C07K 16/30; C12N 5/12; G01N 33/53

(52) U.S. Cl. ............. 424/155.1; 424/1.49; 424/9.1; 424/130.1; 424/133.1; 424/141.1; 424/174.1; 424/178.1; 424/138.1; 435/7.1; 435/7.2; 435/7.21; 435/7.23; 435/326; 435/332; 435/344; 435/344.1; 530/387.1; 530/387.7; 530/388.1; 530/388.2; 530/388.8; 530/388.85; 530/413; 536/23.1; 536/23.5; 536/23.53

(58) Field of Search ................ 435/70.21, 172.2, 435/240.27, 326, 332, 344, 344.1, 7.1, 7.2; 530/388.15, 388.8, 387.1, 387.7, 412, 413; 424/1.49, 130.1, 133.1, 138.1, 141.1, 155.1, 174.1, 178.1, 9.1; 536/23.1, 23.5, 23.53

(56) References Cited

U.S. PATENT DOCUMENTS

| 3,862,925 | 1/1975 | Sarantakis et al. . |
| 4,331,647 | 5/1982 | Goldenberg . |
| 4,349,528 | 9/1982 | Koprowski et al. . |
| 4,444,744 | 4/1984 | Goldenberg . |
| 4,446,240 | 5/1984 | Nerenberg . |
| 4,460,561 | 7/1984 | Goldenberg . |
| 4,485,093 | 11/1984 | Runge . |
| 4,522,918 | * 6/1985 | Schlom et al. .................... 436/548 |
| 4,569,788 | 2/1986 | Mulshine et al. . |
| 4,579,827 | * 4/1986 | Sakamoto et al. ................. 436/536 |
| 4,582,797 | * 4/1986 | Trowbridge .......................... 435/68 |
| 4,585,742 | 4/1986 | Bernal . |
| 4,612,282 | 9/1986 | Schlom et al. . |
| 4,645,828 | 2/1987 | Twardzik et al. . |
| 4,677,058 | 6/1987 | Tryggvason et al. . |
| 4,683,200 | 7/1987 | Hirohashi et al. . |

FOREIGN PATENT DOCUMENTS

| 3 329 184 | * 2/1985 | (DE) | C07G/07/00 |
| 3329184 | * 2/1985 | (DE) | 424/92 |
| A 0098162 | 1/1984 | (EP) . | |
| 0118365 | * 9/1984 | (EP) . | |
| A 0118365 | 9/1984 | (EP) . | |
| A0141079 | 5/1985 | (EP) . | |
| 0151030A2 | 8/1985 | (EP) . | |
| A0153114 | 8/1985 | (EP) . | |
| A0160446 | 11/1985 | (EP) . | |
| 0189849A2 | 8/1986 | (EP) . | |
| 1193378 | * 5/1970 | (GB) . | |
| WO-A8101469 | 5/1981 | (WO) . | |

OTHER PUBLICATIONS

Bosslet et al. Cancer Detection and Prevention 6:181–184 (1983).*
Waldmann Science 252:1657–1662 (1991).*
Harris et al. TIBTECH 11:42–46 (1993).*

(List continued on next page.)

Primary Examiner—Phillip Gambel
(74) Attorney, Agent, or Firm—Finnegan, Henderson, Farabow, Garrett and Dunner, L.L.P.

(57) ABSTRACT

Monoclonal antibodies with specificity for membrane-associated antigens and methods of using them in detection of tumor-associated antigens are described.

19 Claims, 4 Drawing Sheets

OTHER PUBLICATIONS

Osband et al. Immunotherapy 11(6):193–195 (1990).*

Dillman Ann. Internal Med. 111:592–603 (1989).*

Hird et al. Genes and Cancer, published 1990 by Wiley & Sons Ltd, chapter 17, ed. Carnet et al. pp 183–189.*

*Electorphoresis, Theory, Techniques, and Biochemical and Clinical Applications* 2 ed., Oxford Science Publications p. 98 (1986).*

Dillman J Clin Oncology 12: 1497–1575, 1994.*

Bosslet et al. Cancer Immunol. Immunother 23: 185–191, 1986.*

Lembersky Semiwars in Oncology 18(Suppl.) :39–46, 1991.*

ATCC Cell Lines and Hybridoms, 8th Edition 1994 American Type Cultures Coucerow, Rockville MD pp. 59, 266, 311.*

Hand et al, *Cancer Research*, 45, 833–840, 1985.*

Talalay, P., et al., "Chromogenic Substrates, II. Phenolphthalein Glucuronic Acid as Substrate for the Assay of Glucuronidase Activity," J. Biol. Chem., 166:757–772 (1946).

Conchie, J., et al., "Mammalian Glycosidases, Distribution in the Body," Biochem., 71:318–325 (1959).

Davies, P., et al., "The Quantitative Estimation of Pinocytosis Using Radioactive Coloidal Gold," Biochemical and Biophysical Research Communications, 52(2) :627–634 (1973).

Lieber, M., et al., Establishment of a Continuous Tumor–Cell Line (PANC–1) From a Human Carcinoma of the Exocrine Pancreas, Int. Cancer, 15:741–747 (1975).

Bosslet, K., et al., "Monoclonal Murine Antibodies with Specificity for Tissue Culture Lines of Human Squamous–Cell Carcinoma of the Lung," Cancer Detection and Prevention, 6:181–184 (1983).

Herlyn, D., et al., "Inhibition of Human Tumor Growth by IqG2a Monoclonal Antibodies Correlates with Antibody Density on Tumor Cells," J. Immunology, 134(2) :1300–1304 (Feb. 1985).

Brown, J., et al., "A Microassay for Antibody Binding to Tumor Cell Surface Antigens Using $^{125}$–Labelled Protein A from *Staphylococcus Aureus*," J. Immunological Methods, 15:57–66 (1977).

Heyderman, E., "Immunoperoxidase Technique in Histopathology: Applications, Methods and Controls," J. Clinical Pathology, 32:971–978 (1979).

Bosslet, K., et al., "Molecular Characteristics of Two Lung Carcinoma Cell–Line Associated Membrane Antigens," Behring Inst. Mitt, 74:27–34 (1984).

Meeting Highlights, "Breast Cancer, Epithelial Cells, and Extracellular Matrix," JNCI, 73(4) :999–1001 (Oct. 1984).

Wilson, B., et al., "Human Melanoma–associated Antigens Identified with Monoclonal Antibodies," La Ricerca Clin. Lab., 12:517–538 (1982).

Loop, S., et al., "Human Tumor–associated Antigens, p155 and p210, Detected by Monoclonal Antibodies," Biological Abstracts, vol. 73, Heft 1, p. 431, col. 2, Abstract No. 4132 (1982) ; abstract, Int. J. Cancer, 27(6) :775–782 (1981).

Wilson, B., et al., "Distribution and Molecular Characterization of a Cell–Surface and a Cytoplasmic Antigen Detectable in Human Melanoma Cells with Monoclonal Antibodies," Abstract, Int. J. Cancer, Band 28, pp. 293–300 (1981), abstract, p. 293.

Johnson, J., et al., "Surface Antigens of Human Melanoma Cells Defined by Monoclonal Antibodies, I. Biochemical Characterization of Two Antigens Found on Cell Lines and Fresh Tumors of Diverse Tissue Origin," Eur. Journal Immunology, 11:825–831 (1981).

Houghton, A., et al., "Surface Antigens of Melanocytes and Melanomas," J. Exp. Med., 156:1755–1766 (1982).

Klapdor, R., et al., "Experimental and Clinical Studies with the New Monoclonal Antibody 494/32 in Pancreatic Carcinomas," Digestion, 35(1) 1986.

English Translation of DE 3 329 184.

Mitchell, K., "A Carcinoembryonic Antigen (CEA) Specific Monoclonal Hybridoma Antibody that Reacts only with High–Molecular–Weight CEA," Chemical Abstracts, 94(17) :577, abstract No. 137538s (1981).

Accolla, R., et al., "Monoclonal Antibodies Specific for Carcinoembryonic Antigen and Produced by Two Hybrid Cell Lines," Proc. Natl Acad. Sci. (USA), 77(1) :563–566 (1980).

Wunderlich, M., et al., "Effect or Adjuvant Chemo– or Immunotherapy on the Prognosis of Colorectoal Cancer Operated for Cure," Br. J. Surg. Suppl. :S107–S110 (1985).

Morrison–Plummer, et al., Journal of Immunological Methods, 64:165–178 (1983)

Cuttitta, et al., Proc. Natl. Acad. Sci., 78(7) :4591–4595 (1981).

Kohler, et al., Nature, 256:495–497 (1975).

Hand, et al., Cancer Research, 45:833–840 (1985).

Magnani, et al., Cancer Research, 43:5489–5492 (1983).

Wise, et al., Infection and Immunity, 41(3) :1332–1339 (1983).

Schmiegal, et al., Cancer Research, 45:1402–1407 (1985).

Chin, et al., Cancer Research, 45:1723–1729 (1985).

Yuan, et al., Cancer Research, 45:6179–6187 (1985).

Kohler et al., Eur. J. Immunol., 6:511–519 (1976).

Bosslet et al., Br. J. Cancer, 56(4) :516 (1987).

Schulz et al., Br. J. Cancer, 56(4) :516 (1987).

Kubel et al., Br. J. Cancer, 56(4) :528 (1987).

Campbell, Monoclonal Antibody Technology, pp. 66–100, 120–215 (Elsevier) (1985).

* cited by examiner

REACTIVITY OF Ab 1-17 WITH CELLS IN VITRO

| CELLS TESTED | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| LUNG TUMOR CELL LINES | | | | | | | | | | | | | | | | | |
| CaLu-1 | + | + | + | | | + | + | + | + | + | + | | | | | – | |
| E-14 | + | – | – | + | + | + | + | + | + | + | – | – | – | – | – | | + |
| B 109/4 | + | + | | – | + | | | – | – | – | | – | – | | – | – | – |
| A 549 | + | + | + | | | | | + | – | – | – | – | | | | | – |
| Oat 75 | + | + | – | + | – | + | + | + | – | + | – | – | – | + | + | – | + |
| SHP-77 | + | + | – | + | | | + | + | + | | – | + | | | | – | |
| Chago | + | – | – | + | + | – | – | | + | + | – | – | | – | – | – | + |
| Bro-Ca-Hoff | + | + | – | – | + | | – | | – | + | – | – | | | | – | |
| PANCREAS TUMOR OR CELL LINES | | | | | | | | | | | | | | | | | |
| Pa Tu II | + | + | – | – | – | – | + | – | – | – | – | + | – | – | – | + | + |
| | | | | | | | | | | | | | | | | | – |
| Pa Tu III | | + | – | + | | – | – | + | – | + | | + | – | | | – | – |
| MIA-Pa-Ca 2 | + | + | – | – | – | + | – | – | – | – | – | – | – | – | – | – | – |
| Panc-1 | + | + | – | + | – | + | + | – | | – | – | – | – | – | – | – | – |
| GYNECOLOGICAL TUMOR CELL LINES | | | | | | | | | | | | | | | | | |
| Bewo | + | – | + | + | + | + | + | | – | | | – | – | + | + | – | + |
| HeLa | + | + | | + | – | + | + | – | – | – | – | – | – | + | + | – | + |
| Pa-1 | + | + | + | + | – | + | – | – | + | – | – | – | | – | – | – | + |

FIG. 1A

| CELLS TESTED | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| NORMAL LYMPHOID CELLS | | | | | | | | | | | | | | | | | |
| Lymphocytes | + | + | − | − | − | − | − | − | − | − | − | ± | − | − | − | ± | − |
| Monocytes | + | + | − | − | − | − | − | − | − | − | − | − | − | − | − | ± | − |
| Granulocytes | + | + | − | − | + | − | − | − | − | − | − | − | − | − | − | − | ± |
| Erythrocytes | − | − | − | − | − | − | − | − | − | − | − | − | − | − | − | − | − |
| Bone marrow | + | + | − | − | + | − | − | − | − | − | − | − | − | − | − | + | |
| NORMAL HUMAN FIBROBLASTS | | | | | | | | | | | | | | | | | |
| LL-29 | + | + | | − | − | | − | − | − | | − | − | | − | − | − | − |
| Hu-Fi-Br 32 | + | + | + | − | − | − | − | − | − | | − | − | − | − | − | | |
| Hu-Fi-Br 43 | + | + | | − | − | | − | − | − | | − | − | | − | − | − | − |
| Hu-Fi-Br 47 | + | + | | − | − | | − | − | − | | − | − | | − | − | | |
| Hu-Fi-Br 16 | + | + | + | − | − | − | | − | − | − | − | − | − | − | − | − | |
| Hu-Fi-Mel-1 | + | + | + | − | − | − | − | − | − | | − | − | | − | − | | |
| Hu-Fi-Mag-13 | + | + | | − | − | − | − | − | − | − | | − | − | | − | − | |
| ANIMAL CELLS | | | | | | | | | | | | | | | | | |
| Vero | − | + | − | − | − | − | − | − | − | − | − | | − | − | − | + | − |
| Greyhound | − | − | − | − | − | − | − | − | − | − | − | | − | − | − | − | − |
| BHK | − | − | − | − | − | − | + | − | − | − | | − | − | − | − | − | |
| Rat fibroblast | − | − | − | − | − | − | − | − | − | − | | − | − | − | − | − | |
| Mouse fibroblast | − | − | − | − | − | − | − | − | − | − | | − | − | − | − | − | |

FIG. 1B

| CELLS TESTED | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| MELANOMA CELL LINES | | | | | | | | | | | | | | | | | |
| Mel-ULF | + | + | − | + | − | + | + | − | ± | | − | + | − | + | − | + | + |
| Mel-RPMI | + | + | − | + | − | + | + | − | + | | | − | − | − | + | − | + |
| Mel-51-2 | + | + | − | + | − | − | − | − | ± | | − | − | − | − | − | − | + |
| Mel-21-c-48 | + | + | − | + | + | − | + | − | + | | + | − | + | + | − | + | + |
| UNRELATED TUMOR CELL LINES | | | | | | | | | | | | | | | | | |
| ZR-75-1 | + | + | − | | − | + | + | − | | | − | | | + | − | − | |
| MCF-7 | + | + | − | | + | − | − | − | | | − | | | − | − | − | − |
| Mamma-Ca-12 | + | | − | | − | + | + | | | | | | | + | − | | |
| Colon-Ca-Ax | + | | − | | | | − | | | | − | | | − | | − | − |
| Colon-Wi | + | + | − | − | − | − | − | | − | − | − | | | − | − | − | − |
| HT-1080 | + | | | | | | | | + | | | | | − | | | |
| Leiomyo-sarcoma | | + | + | | | | | | | | | | | | | | |
| Hyper-nephroma TUW | | | | | | | | | | | | | | − | | | |
| IMR 32 | + | − | − | | − | − | | − | − | − | | | | − | − | − | − |
| Raji | + | | − | | | − | − | − | | − | | | | − | | − | − |
| Daudi | + | | − | | | − | − | − | | | | | | − | | | − |
| 1788 | + | | − | | | − | − | | | − | | | | | | | − |
| 6666/1 | + | | − | | − | − | − | − | | − | | | | − | | − | − |
| Immunocytoma | + | | − | | | − | + | − | | | | | | | | − | − |

FIG. 1C

\+ = SIGNIFICANT POSITIVE REACTION IN AN INDIRECT IMMUNOFLUORESCENCE ASSAY, IN RADIOIMMUNOASSAY AND IN CYTOFLUOROMETRIC ANALYSIS.

± = WEAKLY POSITIVE REACTION WITH PART OF THE POPULATION TESTED

\- = NO SIGNIFICANT REACTION

FIG. 1D

MONOCLONAL ANTIBODIES WITH SPECIFICITY FOR MEMBRANE-ASSOCIATED ANTIGENS

This application is a continuation of U.S. Ser. No. 08/134,869, filed Oct. 12, 1993, now abandoned, which is a continuation of U.S. Ser. No. 07/967,563, filed Oct. 28, 1992, now abandoned, which is a continuation of U.S. Ser. No. 07/544,651, filed Jun. 27, 1990, now abandoned, which is a continuation-in-part of U.S. Ser. No. 07/425,449, filed Oct. 23, 1989, now abandoned, which is a continuation of U.S. Ser. No. 07/223,773, filed Jul. 25, 1988 now abandoned, which is a continuation of U.S. Ser. No. 07/080,248, filed Jul. 27, 1987, now abandoned, which is a continuation of U.S. Ser. No. 06/639,310, filed Aug. 10, 1984, now abandoned; and a continuation-in-part of U.S. Ser. No. 07/418,722, filed Oct. 3, 1989, now abandoned, which is a continuation of U.S. Ser. No. 07/246,011, filed Sep. 14, 1988, now abandoned, which is a continuation of U.S. Ser. No. 06/729,578, filed May 2, 1985, now abandoned; and a continuation-in-part of U.S. Ser. No. 07/523,835, filed May 1, 1990, now abandoned, which is a continuation of U.S. Ser. No. 07/387,444, filed Jul. 31, 1989, now abandoned, which is a continuation of U.S. Ser. No. 07/261,925, filed Oct. 25, 1988, now abandoned, which is a continuation of U.S. Ser. No. 07/129,896, filed Nov. 24, 1987, now abandoned, which is a continuation of U.S. Ser. No. 06/772,446, filed Sep. 4, 1985 now abandoned, and a continuation-in-part of U.S. Ser. No. 07/565,166 filed Aug. 10, 1990 now abandoned, which is a continuation of U.S. Ser. No. 07/223,734, filed Jul. 22, 1988, now abandoned, which is a continuation of U.S. Ser. No. 06/901,873, filed Aug. 29, 1986, now abandoned; and a continuation-in-part of U.S. Ser. No. 07/456,199, filed Dec. 20, 1989, now abandoned, which is continuation of U.S. Ser. No. 07/203,637, filed Jun. 3, 1988, now abandoned, which is a continuation of U.S. Ser. No. 07/090,604, filed Aug. 28, 1987, now abandoned.

The invention relates to monoclonal antibodies which bind to defined membrane-associated antigens. These antibodies can be used as diagnostic aids, active compounds, or as carriers of active compounds.

In addition, it is known, for example from "Mechanisms of Tumor Immunity," Gree et al., eds., John Wiley and Sons, N.Y., 1977, page 196, that attempts have already been made to treat tumorous diseases by inoculation with tumor cells which have been modified by freezing and thawing, freeze-drying, pressure or homogenization. Subcellular fractions or cell extracts have also been used for this purpose. However, as of yet no vaccine against a tumorous disease has been disclosed. Thus, the invention further relates to a process for the preparation of therapeutic agents from tumor cells for the therapy of tumorous diseases, to a therapeutic agent of this type, and to its use for the therapy of tumors.

The invention also relates to the use of monoclonal antibodies (MAB or Ab) or other ligands which have the property of binding to pancreatic carcinoma cells and of blocking at least one of the following cellular functions: pinocytosis of colloidal gold, production of superoxide anion or release of enzymes, especially of neutral proteases, very especially collagenase or elastase, of growth factor, colony-stimulating factor, erythropoietin, fibroblast growth factor, tumor angiogenesis factor or transforming growth factor, for tumor therapy. The molecules designated as ligands are not monoclonal antibodies but they also bind to pancreatic carcinoma cells and inhibit their cellular functions, for example, certain hormones.

Processes suitable for the preparation of monoclonal antibodies of these types are described in European Patent A-0 160 897, in German Offenlegungsschrift 33 29 184 and in German Patent Application 35 31 301 (filed on Sep. 2, 1985). The technique of immunization with defined isolated antigens and the production of antibodies to antigens of these types are known. Immunization with unpurified antigenic material, and the selection of those antibodies which recognize a particular component in a mixture of antigens of this type are also known.

In the attempt to induce antibodies of these types, it has been possible to select monoclonal antibodies which, under non-reducing conditions, react with the following protein antigens or particular epitopes on these protein antigens: antigen 1: MW 33 KD±3, antigen 2: MW 134 KD±3, antigen 3: MW 80 KD±3, antigen 4: MW 55 KD±3, antigen 5: MW 60 KD±3, antigen 6: MW 54 KD±3, antigen 7: MW 260 KD±3, antigen 8: MW not determinable, antigen 9: MW not determinable, antigen 10: MW 143 KD±3, 119 KD±3, antigen 11: MW 178 KD±3, antigen 12: MW not determinable, antigen 13: MW 34 KD±3, antigen 14: MW 195 KD±3, antigen 15: MW 44 KD±7, antigen 16: MW 43 KD±3, and antigen 17: MW 130 KD±3. It has also been possible to select monoclonal antibodies which, under non-reducing or reducing conditions, react with the following protein antigens or particular epitopes on these protein antigens: antigen 18: MW 72±3 KD, under non-reducing or reducing conditions, antigen 19: MW>200 KD under non-reducing conditions, antigen 20: three glycoproteins of MW 180±10 KD, MW 95±10 KD and 55±10 KD under non-reducing or reducing conditions, and antigen 21: MW>200 KD under non-reducing conditions. These antigens and antibodies are defined in greater detail in the descriptions and examples which follow.

The epitopes on antigens 1–21 which are recognized by Ab 1–21 differ in their sensitivity to treatment with dithiothreitol (50 mmol/l, 2 h, 37° C.): the epitopes of Ag 1, 2 and 15 are modified by the above treatment, while those of Ag 4, 10 and 14 remain unmodified.

The antigens 4, 8, 9 and 10 are mycoplasma antigens which are associated with the cell lines described in the table. The remaining antigens are human cell lines cultured in vitro, cell extracts or extracts of human tissues. Permanent human cell lines, in particular the CaLu-1, Chago, Oat 75, PaTu II and Bewo cell lines, are preferred. It is also possible to use Ag 1–Ag 21 to induce Ab 1–Ab 21.

BRIEF DESCRIPTION OF THE DRAWINGS

The in vitro specificities of Ab 1–17 are shown in FIG. 1. The monoclonal antibodies against antigen 11 (and antigen 20), antigen 3 and antigen 7 are designated BW 250/183, BW 431/26, and BW 494/32 respectively. The cDNA sequences for the variable regions of these antibodies are shown in FIGS. 2, 3, and 4 respectively.

Monoclonal antibodies BW 250/183 and BW 494/32 were deposited in the DSMZ-Deutsche Sammiung von Mikroorganismen und Zelikulturen GmbH, Mascheroder Weg 1b, D-38124 Braunschweig, Germany on Sep. 15, 1999 and given Accession Nos. DSM ACC2412 and DSM ACC2410 respectively. Monoclonal antibodies BW 431/26 and BW 495/36 were deposited in the same depository on Oct. 19, 1999 and given Accession Nos. DSM ACC2414 and DSM ACC2415 respectively.

To form the antibodies of the present invention, mammals, preferably mice, are immunized intraperitoneally with $1 \times 10^6 – 10^8$ cells, but preferably $10^7$ cells, of a cell line of the types described herein (days 0–120, but preferably on days 0 and 7) and, after 1–150 days, but preferably on day 11, the spleen cells from such animals are fused with the X63 Ag 8653 cell line. Examples of these procedures are set forth in The Journal of Immunology 173, 4, 1548–1550, 1979 and Nature 256, 495–497, 1975.

The hybridomas resulting after 3 weeks are tested for antibodies of the desired specificity. In this case, a panel of 30 cell lines cultured in vitro, human peripheral blood cells and human bone marrow were tested for reactivity with the antibodies by means of indirect immunofluorescence (Behring Inst. Mitt. 59, 64–70, 1976) and cell-sorter analysis (Acta Cytol. 19, 374–377, 1975), (Proc. Natl. Acad. Sci. USA 77/8), 4914–4917, 1980).

Surprisingly, among the hybridoma supernatants which were tested, there were some which contained antibodies with the interesting specificities described above. The hybridomas secreting these antibodies were cloned using a micromanipulator, and the monoclonal antibodies obtained from these hybridoma clones were used for the immunochemical characterization of the antigen recognized by them.

For this purpose, cell ghosts (Hybridoma, 1, 4, 413–421 (1982)), which are obtained from tissue culture cells, are solubilized using a detergent, ultracentrifugation is carried out and the mixture of antigens thus obtained is separated by electrophoresis under non-reducing conditions on SDS-polyacrylamide gel (10 g/100 ml acrylamide/0.026 g/100 ml bisacrylamide) (Nature, 127, 680–685 (1970)). Then, all the antigens thus separated were transferred from the SDS gel to a nitrocellulose filter by electro-blotting (Proc. Natl. Acad. Sci. USA, 76, 4350–4354 (1979)). Then the reaction between the antigens immobilized on the nitrocellulose filter and the specific antibodies is carried out (Hoppe-Seylers Z. Physiol. Chem. 363, 1133–1140 (1982)). The binding of this antibody is demonstrated by reaction with $^{125}$I-protein A and autoradiography of the filter. The molecular weight is determined by comparison with commercially available markers.

Preparative purification of the appropriate antigens is carried out by affinity chromatography. Nitrocellulose paper (15×15 cm)(Hoppe-Seylers Z. Physiol. Chem. 363, 1133–1140 (1982)) is moistened with phosphate-buffered saline (PBS, pH 7.2) and then incubated with purified monoclonal antibody protein (1 h, 4° C., 30 ml, 1–100 mg protein/ml). Then the unbound protein is removed by washing in 500 ml of PBS. After incubation of the filter in 3 g/100 ml BSA (bovine serum albumin) and 0.05 g/100 ml Tween 20 in PBS, pH 7.2, (blocking) at 40° C. for 1 h, the filter is washed 3 times with PBS and then incubated with unpurified cell extracts which are dissolved in 0.5% sodium deoxycholate and 20 mM phenylmethylsulfonyl fluoride in PBS at 4° C. for 1 h.

The unbound material is removed by washing 3 times with PBS. The specifically bound antigen is detached by incubation of the filter in 1–9 M $NH_4SCN$, preferably 6 M $NH_4SCN$, in PBS for 5 to 30 minutes, preferably 15 minutes, at 4° C. The antigen thus purified can be used after removal of the $NH_4SCN$ (by gel chromatography dialysis) as an immunogen or for other purposes.

The monoclonal antibodies characterized on the basis of their reactivity with Ag 1 and Ag2 can be used as in vitro diagnostic aid to distinguish between cells derived from solid human tissue and animal cells. Furthermore, they can be used as positive control for human tissue in immunohistology and to distinguish from animal tissue. Moreover, in combination with active compounds, Ab1 to Ab17 can be used to target a site of action, for example in autologous bone marrow transplantation. The use of these antibodies to detect the corresponding antigen in body fluids represents a possible diagnostic use of the antibody. The antibodies can be used in a concentration of from 0.01 mg to 1 mg/ml.

A. A TUMOR THERAPEUTIC AGENT AND A PROCESS FOR ITS PREPARATION

As stated above, the invention also relates to a process for the preparation of a therapeutic agent from tumor cells for the therapy of tumorous diseases, and to a therapeutic agent of this type. We have found, surprisingly, that cells, from human tumors or from cell aggregates obtained from human tumors, which have been freeze-dried or treated with an aldehyde, carry antigens which are bound by the monoclonal antibodies described in German Offenlegungsschrift 3,329,184, and thus can be used as a therapeutic agent for the treatment of tumorous diseases. When used in this context, a "therapeutic agent" is to be understood to be an agent which may be suitable both as a prophylactic and for the treatment of a manifest disease.

Thus, the invention relates to a therapeutic agent for the treatment of a tumorous disease, containing human cells which have been dried or stabilized by a chemical treatment and which carry antigens which are bound by the monoclonal antibodies described in German Offenlegungsschrift 3,329,184, that is, those antibodies that recognize antigens or epitopes on the antigens selected from the group consisting of antigens 1–21.

One advantage of a therapeutic agent of this type compared with the use of unmodified cells is that unmodified cells are not stable, so that they have to be prepared fresh each time. Moreover, for this reason, they cannot be standardized.

The invention furthermore relates to a process for the preparation of a therapeutic agent for the treatment of a tumorous disease, which comprises the drying or stabilization, by a chemical treatment, and the processing to a therapeutic agent, neuraminidase being added where appropriate, of human tumor cells which carry antigens which are bound by the monoclonal antibodies described in German Offenlegungsschrift 3,329,184.

The invention also relates to a process for the preparation of a therapeutic agent for the treatment of a tumorous disease, which comprises the isolation, by means of a monoclonal antibody described in German Offenlegungsschrift 3,329,184, of an antigen from human cells and its processing to a therapeutic agent, neuraminidase being added where appropriate.

The possibility of potentiating an immune response by neuraminidase is disclosed in German Offenlegungsschrift 2,620,649.

The cells which can be used within the scope of the invention are obtained from tumors by known cell culture processes. Cells which have been obtained from such cultures by mechanical or enzymatic means and have, where appropriate, been inactivated with mitomycin C, are dried, preferably freeze dried, or tested with an agent known to those skilled in the art as a stabilizing agent for organic tissue, preferably a monoaldehyde or dialdehyde having 1 to 6 carbon atoms.

The agents which are particularly suitable for chemical stabilization and fixation include, in particular, bifunctional compounds, that is to say those which contain two groups which can react with functional groups on the biological material—in other words can "crosslink" it. Examples of these are dialdehydes, in particular aliphatic dialdehydes having 2–8 carbon atoms. However, monoalkanals having 1–4 carbon atoms, such as formaldehyde, which can undergo bifunctional reactions, as well as bifunctional imino esters, such as suberimidate, isocyanates or isothiocyanates, are also suitable for this purpose.

It is also possible for the so-called tanning agents such as, for example tannic acid and its derivatives, or chromium salts, to be used as agents which can stabilize biological material. Sulfosalicylic acid is also suitable.

In general, the cells are in the form of cell aggregates or single cells. It is also possible to use cell fragments or antigens isolated from the tumor cells. Antigens of this type can be obtained from tumorous tissue from patients, as well as from human tumors which grow in immunodeficient animals, and can be used.

Defined antigens are obtained from the tumor cells or fragments thereof using the monoclonal antibodies described in German Offenlegungsschrift 3,329,184.

Examples of antigens of this type are CEA, (carcinoembryonic antigen, J. Exp. Med (1965), 122, 467), and NCA, (non specific crossreacting antigen; J. Immun. (1973) III, (1926)), which can be isolated from the tumor cells by immunoadsorption chromatography. For this purpose, the monclonal antibodies described in Table I of German Offenlegungsschrift 3,416,774 are covalently bound as purified proteins, to CNBr-activated sepharose 4B, and the antigens (CEA, NCA) recognized by these monoclonal antibodies, are isolated from DE-TA colon carcinoma cell extracts. A suitable process is described in the Pharmacia book "Affinity Chromatograpiy, Principles and Methods", 12–18 (1979), summarized on page 15.

An antigen of this type obtained using monoclonal antibodies can be used as a therapeutic agent, for example as active compound in vaccines against a disease which is caused by the tumor cells from which the antigen was obtained.

Quality control of a material which is to be used as a vaccine is carried out by, for example, typing with monoclonal antibodies, or by fractionation of the total cellular proteins using SDS-polyacrylamide gel electrophoresis or isoelectric focusing (1st dimension) combined with SDS-polyacrylamide gel electrophoresis (2nd dimension) followed by staining of the gel (silver stain).

The antigenic material is preferably administered intradermally, preferably by the checkerboard vaccination method (Cancer Immunol. and Immunother. 6, 47–58 (1979), in particular page 48 in combination with an adjuvant, in particular neuraminidase (German Offenlegungsschrift 2,620,640).

A vaccine of this type is preferably used for certain stages of colon carcinoma (Duke C) and for other tumors which carry antigens or epitopes which are present in the vaccine. Other tumors of this type are solid tumors, for example carcinomas of the pancreas, of the stomach, of the breast and of the lungs. The vaccine can be administered parenterally or orally. The antigens can be administered, dissolved or suspended in physiological saline, preferably intradermally in PBS.

Two tests were carried out to assess the stability of the antigenic composition of the vaccine:

a) The Terasake IIF Assay (indirect immunofluorescence using tumor cells which grow in the wells of the Terasake microtiter plate) with monoclonal antibodies of various specificities. It is possible by means of this test to measure the expression of membrane antigens on intact tumor cells, against which a number of monoclonal antibodies are available (Cancer Detection and Prevention 6, 181–184, 1983). It was possible by this means to detect drastic changes to the DE-TA cell membrane during cultivation;

b) solubilization of the total cellular proteins using a detergent (Hybridoma 1, 413–421, 1982) followed by SDS-poly acrylamide gel electrophoresis combined with a silver stain (Anal. Biochem. 105 361–363, 1980). The combination of these techniques ensures that no significant changes in the total protein content of the DE-TA cell line have occurred.

B. DETAILED DESCRIPTION OF PREFERRED ANTIGENS, EPITOPES, AND MONOCLONAL, ANTIBODIES

1. Antigen 18

Antigen 18 carries an epitope which, on the cell membrane of the Oat-75 small-cell lung carcinoma cell line (Cancer Research (1977), 37, 3088–3095) and on the tumors derived from Oat-75 and transplanted onto the nude mouse, is accessible to the MAB 278/97 of the IgG, isotype, that is to say the MAB binds to the native Oat-75 cell line, or the corresponding transplanted tumor tissue, carrying the epitope. It has not been possible to detect the epitope either on another small-cell lung carcinoma cell line (SHP-77) or on 5 other non-small-cell lung carcinoma cell lines (Calu-1, E-14, B109, A549, Chago, Bro-CaHof; ATCC lines). Moreover, it has not been possible to detect the epitope on 5 pancreatic tumor cell lines (PaTu-I, II, II1, MIA Pa-Ca-2, PANC-1), 2 gynecological tumor cell lines (HeLa, PA-1), 3 other, non-related carcinoma cell lines (MCF-7, MDA-1, Co-Wi), 6 human fibroblast lines, 3 non-human cell lines (Vero, rat fibroblasts, NMRI mouse fibroblasts) or leukocytes from peripheral human blood.

Furthermore, the epitope is undetectable on 12 lung carcinomas transplanted onto the nude mouse and 4 transplanted pancreatic tumors as well as 7 lung carcinomas taken directly from the patient, one carcinoma of stomach and one of the colon, 5 normal lung tissues, or one sample in each case of normal tissue from the pancreas, stomach, colon and thyroid.

Following fixation with formaldehyde and embedding in paraffin of the Oat-75 tumor transplant, the epitope, which is detectable on cryopreserved material, is modified such that MAB 278/97 no longer binds.

2. Antigen 19

Antigen 19 carries an epitope which, on the cell membrane of the Oat-75 small-cell lung carcinoma cell line and on the tumors derived from the Oat-75 and transplanted onto the nude mouse, is accessible to MAB 278/105 of the $IgG_3$ isotype. The epitope can be detected in vessels, for example in cryostat sections as well as on materials from normal and tumor tissue which have been treated with formaldehyde and embedded in paraffin.

In this case, it is found preferentially in endothelial cells, but it can also be found in extracellular regions such as, for example, in parts of the basal membrane or the internal elastic lamina. It is undetectable in megakaryocytes, but it is detected in the capillary loop endothelium of the glomeruli (in contrast to F VIIIR:AG). The epithelium in Bowmann's capsule is unreactive.

By its nature, it is particularly concentrated in tumors of the vascular system. Moreover, the epitope is detectable in, for example, endothelial cells of human umbilical cords and on the cell membrane (after fixing with glutaraldehyde) as well as in the cytoplasm (punctate components around the nucleus and intra-cytoplasmic granular distribution). Furthermore, endothelial cells of human iliac crest veins express the epitope while, in contrast, the epitope is undetectable in endotlhelial cells of the pulmonary aorta of cattle. The epitope is undetectable on the cell membrane of leukocytes from human peripheral blood.

In addition to the resistance of the epitope in tissue to fixation with formaldeyhyde and embedding in paraffin, which was indicated above, it is also resistant to treatment with neuraminidase but is sensitive to periodic acid oxidation. On the basis of its properties, MAB 278/105 appears to be suitable for the diagnosis of tumors derived from the endothelium and for chronic inflammations.

3. Antigen 20

Antigen 20, because of its strong cross-reaction with heterologous anticarcinoembryonal antigen antisera, is similar to the carcinoembryonal antigen (CEA) which was isolated in 1965 by Gold and Freedman (J. Exp. Med. (1965), 122, 467). A relatively large number of epitopes are located on this complex glycoprotein, and these also occur on other molecules which are not identical to CEA. These are the antigens $NCA_2$ (non specific crossreacting antigen; J. Immun. III (973), 1926), $NCA_1$ (non-specific crossreacting antigen; Ann. N.Y. Acad. Sci. (1975), 259, 389), BGP-I (Int. J. Cancer (1976), 17, 588) and $CEA_{low}$ (Scand. J. Immunol. (1978), Vol. 8, Suppl. 8, 423–428).

Seven new epitopes have been discovered on antigen 20. The antigen has been detected by immunoprecipitation in, for example, a colon carcinoma cell line (DE-TA) and its molecular weight there is significantly lower than the molecular weights reported in the literature for CEA.

4. Antigen 4

Antigen 4 carries an epitope which, on the cell membrane of the Pa-Tu-I pancreatic carcinoma cell line and on the tumors of the Pa-Tu-I cell line transplanted onto the nude mouse, is accessible to MAB 406/14 of the $IgG_1$ isotype (light k chain). The MAB reacts with pancreatic tumor tissue which has been cryopreserved or fixed with formaldehyde and embedded in paraffin, and with the duct epithelium of the healthy and inflamed pancreas and with colon carcinomas. The MAB reacts weakly with the alveolar epithelium of normal lung, and does not react with normal endocrine and exocrine pancreatic tissue or with leukocytes from human peripheral blood. The MAB reacts weakly with the intestinal crypts.

5. Monoclonal Antibodies I–VII

The invention also relates to monoclonal antibodies which recognize a protein antigen which has a molecular weight of approximately 72±3 KD under non-reducing or reducing conditions, or a glycoprotein antigen which has a molecular weight>than 200 KD under non-reducing conditions, and which is not identical to F VIIIR:AG, or 8 defined epitopes on three glycoprotein antigens which have a molecular weight of 180±10 KD, 95±10 KD or 55±10 KD under non-reducing conditions, or a glycoprotein antigen which has a molecular weight>than 200 KD under non-reducing conditions, and which is not identical to EMA.

These antigens are unambiguously characterized by the occurrence, indicated above, on particular cells and tissues and by the characteristics of the epitopes which occur on these antigens and are defined by the particular MABs.

TABLE 1

| MAB | CEA | $CEA_{low}$ | $NCA_2$ | $NCA_1$ | BGP-I |
|-----|-----|-------------|---------|---------|-------|
| I   | +   | +           | +       | +       | −     |
| II  | +   | +           | +       | −       | −     |
| III | +   | +           | −       | −       | −     |

TABLE 1-continued

| MAB | CEA | $CEA_{low}$ | $NCA_2$ | $NCA_1$ | BGP-I |
|-----|-----|-------------|---------|---------|-------|
| IV  | +   | +           | −       | +       | −     |
| V   | +   | −           | +       | −       | −     |
| VI  | +   | (+)         | −       | −       | −     |
| VII | +   | −           | −       | −       | −     |

The epitopes on the CEA molecules which are recognized by MABs I–VII (See Table 1) differ from the epitopes defined, using monoclonal antibodies, in Mol. Immunol. (1982), 19, 12, 1641–1648 and European Patent Appl. 0,098,162 A2 (1983) by differences in the distribution on the abovementioned molecules.

6. Monoclonal Antibody BW 431/31

The characteristics of MAB VII (BW 431/31) are described in detail below:

MAB BW 431/31 recognizes an allotypical epitope on the CEA (180 KD) purified from human colon, pancreatic, stomach and lung carcinomas. This epitopc is resistant to fixation with formaldehyde and embedding in paraffin of the tissue used for the investigation. Furthermore, the epitope is resistant to periodate oxidation and treatment with neuraminidase.

The epitope can be detected by immunohistological methods in the following human tissues fixed with formaldehyde and embedded in paraffin: 80–90% of the primary tumors of colon carcinoma and the liver metastases resulting from them show a strong membranaceous reaction which increases toward the lumen. In contrast to this, there is no reaction with normal liver tissue surrounding the metastases. An additional significant finding is that there is no significantly detectable reaction by the entire normal colon tissue, including the mucosa. This observation distinguishes MAB BW 431/31 from all the monoclonal antibodies described in the literature, especially from Mab 35 described in Int. J. Cancer (1984) 33,643, which shows a significantly stronger reaction with the outer mucosa and, additionally, with the intestinal crypts. No significant reaction with MAB BW 431/31 is shown by any of the other normal tissues tested, such as normal lung, normal pancreas, inflammed pancreas, normal stomach, normal spleen, tonsils, lymph nodes, and leukocytes from peripheral blood. In addition to the majority of colon carcinomas, about 30–50% of the tested pancreatic carcinomas and about 40–60% of the tested stomach carcinomas showed a marked reaction with BW 431/31.

MAB BW 431/31 is a mouse immunoglobulin of the γ1 isotype associated with a light chain of the κ type. The Fc part of the molecule is able to bind to protein A.

CEA can be isolated in a highly pure form from tissue solubilizates and body fluids using MAB BW 431/31 immobilized on solid carriers.

The CEA thus purified undergoes a change following adsorption onto nitrocellulose, so that the binding of MAB 431/31 is now inefficient. In contrast to this, under identical conditions, on nitrocellulose the epitope on CEA which is recognized by Mab 35 (Int. J. Cancer (1984) 33, 643) remains accessible to Mab 35, so that Mab 35 binds very efficiently. Furthermore, the molecular weight of the MAB BW 431/31 which has been fractionated under non-reducing conditions by SDS-PAGE is significantly below that of Mab 35 (about 7000 KD). This difference in molecular weight of the κ-light chain of Mab BW 431/31 as revealed by SDS-PAGE under reducing conditions (MW of κ-light chain of Mab BW 431/31=25 KD, of Mab 35=29 KD).

MAB VIII recognizes an epitope which is to be found only on a subpopulation of CEA molecules (30%).

7. Monoclonal Antibody 406/14

MAB 406/14 reacts with not only the duct epithelium of the pancreas, but also the duct epithelium of the liver and of the mammary gland, and in the latter case specifically in the apical part of the epithelial cells. Furthermore, in the region of the normal mammary gland, the epithelium of the acini and the coating connective tissue cells in the region of the acini are positive. The mammary sarcomas derived from these mesenchymal cells also have a positive reaction. The coating connective tissue cells represent a mesenchymal component. This reactivity with both mesenchymal and epithelial components distinguishes MAB 406/14 from antibodies which react with the "epithelial membrane antigen" (EMA) (J. Clin. Pathol. (1979) 32, 35).

All the mammary carcinomas derived from the duct epithelium (ductal mammary carcinomas) which have been investigated to date (12/12) show a pronounced cytoplasmic reaction, and some also show a perinuclear reaction with MAB 406/14, as do the mammary carcinomas; (6/6). In addition, the lymph nodes (the tumor cells in them) affected by ductal mammary carcinomas show a strong reaction with MAB 406/14 (6/6). All the squamous cell carcinomas of the lung which have been tested (10/10) show a pronounced cytoplasmic as well as a membranaceous reaction. 6 of 10 tested adenocarcinomas of the lung, 4/8 large-cell carcinomas of the lung and 2/5 small-cell carcinomas of the lung react with MAB 406/14.

Furthermore, MAB 406/14 shows no detectable binding to tissue from normal spleen, lymph nodes or stomach while, in contrast, there is weak binding to the mucosa, some cells of the glands and some parts of the muscle in the region of the normal colon. In addition, the MAB binds to a subpopulation of the tested colon carcinomas (4/17) and exocrine pancreatic carcinomas (11/17). The epitope which ocurs in tissues which are positive to MAB 406/14 is resistant not only to fixation with formaldehyde and embedding in paraffin but also to periodic acid oxidation and treatment with neuraminidase.

One application is the non-invasive detection of lymph node metastases of mammary carcinoma by injection of the radioactively labelled MAB into the interdigital webs, into the draining lymph tracts or intravenously. Additional areas of use are immunoscintigraphy and immunotherapy of, in particular, squamous cell carcinoma of the lung, as well as other histological types of carcinoma of the lung, and ductal mammary carcinoma and certain exocrine pancreatic carcinomas. The detection in body fluids of the epitope defined by MAB 406/14 is a method for the early diagnosis and for monitoring the progress of those tumors which secrete the epitope in amounts which are readily detectable.

The method used for the production of the above-mentioned monoclonal antibodies is described on pages 3, 4 and 5 of German Offenlegungsschrift 3,329,184.

C. PROCESS FOR THE PREPARATION OF THE MONOCLONAL ANTIBODIES

The invention also relates to a process for the preparation of one of the monoclonal antibodies described above, which comprises the immunization of mammals with cells of the Oat-75 cell line, of the Pa-Tu-I cell line or of a CEA-positive adenocarcinoma, or carcinoembryonic antigen (CEA), the removal of spleen cells from an animal immunized in this way and fusion with the cell line X 63-Ag8653 or SP-2, selection of the hybridomas and obtaining of the monoclonal antibodies.

Theimmunogen used for the induction of MAB 278/97 and MAB 278/105 is the Oat-75 cell line, and that for the induction of MAB 406/14 is the Pa-Tu-I cell line. The immunogen used for the induction of the MABs defined by the epitopes on antigen 3 is a CFA-positive adenocarcinoma of the lung; however, it is also possible to use commercially available CEA.

Mammals, preferably mice, are immunized with cells or antigens of one or more of these cell lines. and the spleen cells from these animals are fused with the X 63 Ag8653 cell line.

It is also possible to remove, for example, human lymphoid cells from tumor patients or healthy subjects, and to carry out vitro immunization and fusion with a human myeloma cell. It is also possible to use the technique of EBV transformation or transfection with DNA (oncogene transfer) in order to stimulate the human lymphoid cells to permanent division.

The resulting hybridomas are tested to find whether they contain antibodies of the desired specificity. Among the hydridoma supernatants tested, there were some which contained antibodies of the specificities described above. The hybridomas secreting these antibodies were cloned, and the monoclonal antibodies obtained from these hydridoma clones were used to carry out immunochemical characterization of the antigen recognized by them. The molecular weight is determined by comparing with commercially available markers. The antigens can be purified by affinity chromatography.

In addition, the binding of the monoclonal antibodies to histological specimens was measured using the indirect immunoperoxidase technique (J. Clin. Pathol. 1979), 32, 971).

Furthermore, the molecular characterization of the antigens, or subpopulations of antigenic molecules, recognized by the monoclonal antibodies was carried out, in addition to the Western blot analysis, by radioimmunoprecipitation (Behring Institute Communications (1984), 74, 27–34), and the epitope analysis for the 180±10 KD CEA, or 95±10 KD and 55±10 KD CEA related molecules was carried out by means of an ELISA under blocking conditions (Clin. Chim. Acta (1983), 135, 13–22, specifically page 15).

The molecular characterization of the epitopes on human tissue which are recognized by the MABs was carried out as described below:

Four to six $\mu$m thick sections of cryopreserved human tissue carrying the appropriate epitopes were dried on the slide (for 30–60 min at room temperature) and then fixed in acetone for 1–2 secs. They were then:

a) for the periodate oxidation, washed in PBS, pH 7.2, containing 1 g/l BSA for 10 min, briefly immersed (rinsed) in PBS, pH 7.2, and incubated with 1 g/100 ml periodic acid in PBS, ph7.2, for 1 hour at room temperature in a humidity cabinet. The sections are then washed 3×5 min in 1 g/l BSA in PBS, pH 7.2, and incubated with normal goat serum, further treated, as in J. Clin. Pathol. (1979) 32, 971, with the MABs which are to be tested, and their binding to the tissue is detected using the indirect immunoperoxidase technique;

b) for the treatment with neuraminidase, the sections were washed 2×10 min in 0.05 M $Na^+$, $Ca^{++}$ acetate buffer, pH 5.5, and incubated for 1 hour with various amounts of Vibrio cholerac neuraminidase (100 mU/ml, 10 mU/ml, 1 mU/ml, 0.1 mU/ml) in the above-mentioned acetate buffer, at room temperature in a humidity cabinet. After washing the sections twice in acetate buffer and twice in PBS, pH 7.2, containing 1 g/l BSA, they are incubated with normal goat serum, further treated, as in J. Clin. Pathol. (1979) 32, 971, with the MABs which are to be tested, and their binding to the tissue is detected using the indirect immunoperoxidase technique.

To test the resistance to formaldehyde and paraffin of the epitope by the particular MAB, the 4–6 um thick cryopreserved tissue sections are replaced by tissue which is fixed in formaldehyde and embedded in paraffin and then sectioned in a microtome, the paraffin is removed (B. Romeis, Mikroskopische Techniken (Techniques of Microscopy) 16th edition, page 145, section 546, 1968) and further treated as described in J. Clin. Pathol. (1979) 32, 971 for the indirect immunoperoxidase technique.

Because of their reactivity with antigen 18, the characterized monoclonal antibodies can be used for the diagnostic recognition of small-cell lung tumors carrying the 72 KD antigen and for differentiating them from other tumors without antigen 18.

The monoclonal antibodies characterized on the basis of their reactivity with antigen 19 can be used for the diagnostic recognition of tissue carrying the >200 KD antigen (endothelial tissues and vascular tumors) and for differentiating it from other tissue without antigen 19.

The monoclonal antibodies defined by their reactivity with 8 different epitopes on the CEA related molecules 180±10 KD, 95±10 KD and 55±10 KD in size can be used for the diagnostic recognition of CEA-positive tissue (for example, colon carcinomas, mammary carcinomas and lung carcinomas).

The monoclonal antibodies characterized by their reactivity with antigen 21 can be used for the diagnostic recognition of tissue carrying the >200 KD antigen (mammary carcinomas) and for differentiating it from other tissue without antigen 21.

Furthermore, all the antibodies described above which recognize antigens can be used to detect in body fluids the antigens which they recognize, or, in the radioactively labelled form, to bind in vivo to the tissue carrying the particular antigen and to detect the antigens (immunoscintigraphy). In addition, these monoclonal antibodies can be used as carriers of active compounds and can be employed for the therapy of malignant diseases. Another possible use is represented by the inhibiting of tumor cell metastasis following in vivo administration and binding of the monoclonal antibodies to antigen-carrying metastisizing tumor cells. In addition, these monoclonal antibodies can, without the presence of other toxins, be toxic for the antigen-carrying tumor cells, or, after binding to the tumor cell membrane, lead to differentiation processes which allow malignant tumor cells to become benign cells.

For diagnostic purposes, the monoclonal antibodies can be used in a concentration of from 0.001 mg/ml to 100 mg/ml, depending on the assay. Therapeutic effects are attained in amounts of 200 mg–100 mg/kg body weight.

D. MONOCLONAL ANTIBODIES AGAINST TUMOR ASSOCIATED GLYCOPROTEINS AND A PROCESS FOR THEIR PREPARATION AND USE

We have succeeded in selecting monoclonal antibodies having advantageous properties. These have the characteristic that they react with particular epitopes on protein antigens, as follows:

MAb 436/15 reacts with a glycoprotein which has a molecular weight exceeding 200 KDA under non-reducing conditions (antigen 22). The epitope recognized by this MAb is resistant to formaldehyde fixation or paraffin embedding in the same way as it is to neuramidase treatment. However, this epitope is destroyed by periodate oxidation. MAb 436/15 belongs to the $IgG_3$ isotype with a kappa chain as the light chain.

MAb 494/32 recognizes an epitope on a glycoprotein (antigen 23) of molecular weight exceeding 200 kDa under non reducing or under reducing conditions, which is resistant both to formaldehyde fixation or paraffin embedding, as well as to neuraminidase treatment. Periodate oxidation results in destruction of this epitope. MAb 494/32 belongs to the $IgG_1$ isotype with a kappa chain as the light chain.

MAb 495/19 and MAb 495/36 recognize an epitope on a glycoprotein (antigen 24) of a molecular weight exceeding 200 KDA under non-reducing or under reducing conditions, which is resistant both to neuraminidase treatment and to periodate oxidation. In contrast to the epitopes on antigens 1 and 2, this epitope is not resistant to formaldehyde fixation or paraffin embedding. MAb 495/19 and 495/36 are of the $IgG_3$ isotype with a kappa chain.

MAb 494/32 and MAb 495/36 are able to promote the ADCC reaction (see for methods: D. Herlyn et al. The Journal of Immunology 134, 2, 1,300–1,304 (1983)).

The invention relates to a monoclonal antibody, which is called MAb 436/15, of the $IgG_3$ isotype with a kappa chain, which antibody reacts with a glycoprotein (antigen 1) which has a molecular weight (MW) exceeding 200 kDa under non-reducing and under reducing conditions, and to two monoclonal antibodies, which are called MAb 495/19 and 495/36, of the $IgG_3$ isotype with a kappa chain, which antibodies react with a glycoprotein (antigen 3) which has a MW exceeding 200 kDa under non-reducing and under reducing conditions.

MAb 436/15 recognizes an epitope on antigen 1, with the following accessibility on human tissues, human tumor xeno transplants on the nude mouse or in vitro cultivated cell lines, where the epitope has been detected in the case of the cell lines by means of an indirect immunofluroescence method on live cells (J. immunol. Methods 1977, 15, 57–66), and in the case of the xenotransplant or human tumor tissue by means of the indirect immunoperoxidase method (J. Clin. Path. 1979, 32, 971–978):

The colon carcinoma cell line DE-TA and the pancreas carcinoma cell line PaTuI show a marked membrane fluorescence. The xenotransplants of the pancreas carcinomas PaTuI and PaTuII and the small-cell xenotransplant of a lung carcinoma B110 show a positive immune staining in particular tissue areas, whereas there is no detectable reaction to the lung carcinoma BroCa17 and the pancreas carcinoma tissue PaTuIII.

The reaction of MAb 436/15 to human carcinomas is with 8 highly differentiated adenocarcinomas of the lung out of 55 other lung carcinomas tested (both secreted product staining and staining of the cytoplasm and membrane). A few squamous cell carcinomas of the lung likewise react. Furthermore, about 50% of colon carcinomas and the liver metastases derived therefrom, about 60% of pancreas carcinomas, 10–20% of the tumor areas in about 4% of ovarian carcinomas (strong reaction with secretion) and a few cells in 50% of mammary carcinomas are reactive.

MAb 436/15 shows no essential binding to lymph nodes, tonsils, peripheral blood leukocytes, normal liver and normal colon. The dysplastic epithelium of the lung, the inter- and intralobular ducts of the pancreas and a few acinar cells, and the gastric glands and a few cells in the spleen show a reaction.

MAb 494/3)2 recognizes an epitope on antigen 2 with the following accessibility on human tissues, human tumor xenotransplants on the nude mouse or in vitro cultivated cell lines, the binding having been detected as before.

The colon carcinoma cell line DE-TA shows a marked membrane fluorescence. The xenotransplants of the pancreas tumors PaTuI and II, I.W. and 14, and the xenotransplants of the colon carcinomas 4 and 5 show a marked cytoplasm and cell membrane reaction.

The reaction of MAb 494/32 to human carcinomas is with about 80% of grade I and II adenocarcinomas of the pancreas, whereas no noteworthy reactions are observed with the grade III pancreas carcinomas. Furthermore, there is immunohistological staining of about 70% of liver metastases of colon carcinomas and about 30% of the primary tumors of colon carcinomas. A few tumor cells in about 40% of lung carcinomas are reactive.

Normal tissue from the lungs, liver, breast, kidneys, spleen and lymph nodes, and bone marrow and connective tissues, as well as muscles and peripherral blood leukocytes, show no noteworthy immune reactions with MAb 494/32. However, the mucus-producing cells of the stomach and of the colon (goblet cells) and a few cells of the outer mucous membrane of the colon do stain. The duct system in an inflamed pancreas shows a positive reaction, whereas the exocrine and endocrine pancreas tissue does not react.

The molecular weight of the antigen defined by MAb 494/32 (above 200 kDa) differs from th a t of the glycoproteiats defined by the MAb AR2–20 and AR1–28, which is 190 kDa (Cancer Res. 1985, 45, 1,723–1,729). Furthermore, the epitope accessibility for MAb 494/32 is such that it preferentially reacts with the highly differentiated adenocarcinomas of the pancreas, whereas the MAb AR2–20 and AR1–28 react with all pancreas carcinomas tested. There are marked differences between MAb 494/32 and the MAb DUPAN-2 (JNCI, 1985, 72, 999–1,003) in the epitope accessibility (DUPAN-2 reacts with all pancreas and gallbladder carcinomas and many glandular tissues) and the neuraminidase resistance (DUPAN-2 recognizes a neuraminidase-sensitive epitope). The MAb C54-0, C1-N3 and C1-P83 which are described in Cancer Res., 1985, 45, 1,402–1,407 differ from MAb 494/32 in respect of the accessibility of the epitopes and the defined antigen (molecular weight of 122 kDa for C54-0).

MAb 495/36 and 495/19 recognize an epitope on antigen 3 with the following accessibility on human tissues, human tumor xenografts on the nude mouse and in vitro cultivated cell lines, a reaction having been detected as before:

The colon carcinoma cell line DE-TA shows a marked membrane fluorescence. All the human tumor xenotransplants tested, such as the bronchial carcinomas BroC-11 GOT-1, MR-21E560Sp, BroCa-33, BroCa-53, B98, the pancreas carcinomas PaTuI, PaTuII and the colon carcinomas Ca 4,5, Le-Met Co. Ca 2, DE-TA, Le-Met Co. Ca 9 and Le-Met Co. Ca. 3 show a strono cytoplasmic and membrane reaction.

On human lung carcinoma tissues MAb 495/36 shows a marked membrane reaction with about 100% of the tested cases of various histologies. Furthermore, about 90% of pancreas carcinomas, liver metastases of colon carcinomas, and ovarian and bladder carcinomas and mammary carcinomas show a strong membrane reaction. No immunohistological staining is found with peripheral blood leukocytes, lymphocytes, spleen, blood vessels, connective tissue or muscle. There is a positive reaction of the mucous membrane and the crypts of the normal colon, the bile duct epithelium in the liver, and the glandular tissue in the stomach. The epithelium of the lung and the exocrine and endocrine pancreas tissue show a strong reaction.

The method used for the production of the above monoclonal antibodies is described in German Offenleoungschrift 3,329,184 on pages 3 to 5.

The invention also relates to a process for the preparation of one of the monoclonal antibodies described above, which comprises immunization of a mammal with cells of the lung carcinoma cell line MR22E572 or of the colon carcinoma cell line DE-TA, removal of spleen cells from an animal which has been immunized in this way, fusion with the cell line X63 Ag8.653, selection of the hybridomas, and obtaining of the MAb.

The immunogen used for the induction of MAb 436/15 is the cell line MR22E572, and that for the induction of MAb 494/32, 495/36 and 495/19 is the DE-TA cell line. Mammals, preferably mice are immunized with cells of one of these cell lines, and the spleen cells from such animals are fused with the X63 Ag8.653 cell line.

The resulting hybridomas are tested for the presence of antibodies of the desired specificity. Among the hybridoma supernatants which are tested there are a few which contain the antibodies having the specificities described above. The hybridomas secreting these antibodies are cloned, and the monoclonal antibodies obtained from these hybridoma clones are used for the immunochemical characterization of the antigen which they recognize. The molecular weight is determined by comparison with commercially obtainable markers. The antigens can be purified by affinity chromatography.

In addition, the binding of the monoclonal antibodies to histological specimens is measured using the indirect immunoperoxidase technique (J. Clin. Pathol., 1979, 32, 971).

Furthermore, the molecular characterization of the antigens or subpopulations of antigenic molecules which are recognized by the monoclonal antibodies is carried out in addition to Western blot analysis by radioimmunoprecipitation (Behring Institute Mitteilungen, 1984, 74, 27–34).

By reason of their reactivity with various epitopes on human tissues, the MAb 436/15, 494/32 and 495/36 or 495/19 can be used for the immunohistological differentiation between epitope-positive and epitope-negative tissues or body fluids The MAbs described above are furthermore able, in a radiolabeled form, to bind to tumors in vivo (436/15, 494/32) and with their aid it is possible to detect early metastases in draining lymph nodes by immunoscintigraphy (495/36, 495/19).

In addition, these monoclonal antibodies can be employed as carriers of active compounds and used for the therapy of malignant diseases. Further possible uses are represented by the inhibition of tumor cell metastasis after in vivo administration or the binding of the monoclonal antibodies to antigen-carrying, metastasizing tumor cells. Furthermore, these monoclonal antibodies may be toxic, without cooperation from other toxins, for the antigen-carrying tumor cells, or may result, after binding to the tumor cell membrane, in differentiation processes which cause malignant tumor cells to become benign cells.

Furthermore, the MAb 494/32 and 495/36 which promote ADCC can be used, in a non-radiolabeled form, for the tumor therapy of epitope-positive tumors after systemic or regional administration.

However, the monoclonal antibodies which have been described can also be used in a labeled form as diagnostic aids or for the analysis of tissues and body fluids and for radio immunoscintigraphiy or as therapeutic agents for radioimmunotherapy or for chemoimmunotherapy.

For diagnostic purposes the monoclonal antibodies are used in a concentration of 0.001 mg/ml to 100 mg/ml, depending, on the test.

Therapeutic effects are achieved in amounts of 200 mg–100 mg/kg of body weight.

Apart from the intact antibodies according to the invention, it is also possible to make use of their products of cleavage by enzymes (in particular papain, plasmin or pepsin), which are prepared by processes known to those skilled in the art, such as, for example, F(ab')$_2$ or Fab.

E. THE USE OF MONOCLONAL ANTIBODIES FOR THE THERAPY OF TUMORS

With regards to the use of monoclonal antibodies for the therapy of tumors, it has been found, surprisingly, that human pancreatic carcinoma cell lines are able to secret lysosomal enzymes, pinocytose colloidal gold and generate superoxide anion, and that these cellular functions can be blocked by binding monoclonal antibodies, in particular 494/32, 495/36, 227/18 or 227/19, to the pancreatic carcinoma cells. MAbs 494/32 and 495/36 are described in the cited patent application whereas others are described in the cited Offenlegungsschrift. In these citations they are designated as follows: 227/18 as AK 2 and 227/19 as AK 16.

One consequence of the attachment of such MAbs, which is followed by blocking of the said cellular functions, is the regression of progressively growing pancreatic carcinomas in patients.

These cellular functions of pancreatic carcinoma cells include the release of, in particular, neutral proteases, very particularly collagenase or elastase, of growth factors, epidermal growth factor, platelet-derived growth factor, colony stimulating factor, erythropoietin, fibroblast growth factor, tumor angiogenesis or transforming growth factor.

Monoclonal antibodies (MAb) which have the property of binding to pancreatic carcinoma cells and of blocking physiological functions, preferably the pinocytosis of colloidal gold, the production of superoxide anion or the release of enzymes, especially of neutral proteases, very especially collagenase or elastase, of growth factors, epidermal growth factor, platelet-derived growth factor, colony stimulating factor, erythropoietin, fibroblast growth factor, tumor aiioi (lenesis factor or transforming growth factor, are accordingly suitable for the therapy of tumors whose cells exhibit these cellular functions. Equally suitable are binding fragments of a MAb of this type, except the Fc fragment, as well as other ligands, that is to say molecules with the property of binding to pancreatic carcinoma cells and of blocking the said functions.

Apart from pancreatic carcinomas examples of tumor cells with relevant secretory properties are carcinomas of the breast, ovarian carcinomas and adenocarcinomas of the lungs.

Hence the invention relates to the use of a monoclonal antibody or of one of its non-Fc fragments or of another lioand, each of which has the property of blocking the following cellular functions of a tumor cell: the pinocytosis of colloidal gold, the production of superoxide anion or the release of enzymes, especially of neutral proteases, very especially collagenase or elastase, of growth factors, epidermal growth factor, platelet derived growth factor, colony-stimulating factor, erythropoietin, fibroblast growth factor, tumor anoiogenesis factor or transforming growth factor from pancreatic tumor cells, for the therapy of tumors.

Tumors which can be treated with such MAbs or other ligands are, preferably pancreatic carcinomas, carcinomas of the breast, ovarian carcinomas or adeniocarciniomas of the lungs, in particular pancreatic carcinomas.

It is possible to use pancreatic carcinoma cell lines, preferably the PANC-1 line (Int. J. Cancer (1975) 15, 741; ATCC CRL 1469), for testing whether the MAbs or ligands bind to pancreatic carcinoma cells.

To select MAbs or ligands which can be used in the manner according to the invention, the inhibition by the MAbs or ligands of the chemiluminescence of cells of a cell line of this type is determined. The determination of the chemi luminescence of cells is a method for detecting the generation of superoxide anion by a cell and for determining the amount thereof.

For this purpose, the tumor cell line is cultured in Dulbecco's minimal essential medium (DMEM) which contains 100 ml/l fetal calf serum and 1 mmol/l glutamine (DMEM-FCS-GLN). This entails the cell line in the confluent state being treated with 2 g/l trypsin and 0.2 g/l EDTA in Puck's saline at 37° C. for 1 minute and, after washing, being transferred in the ratio of 1:20 into DMEM-FCS-GLN. The isolated cells are left to adhere in DMEM in a round-bottomed polystyrene tube, at a cell count of $10^6$ cells, for four hours. After having been washed in DMEM three times, 100 ml of DMEM are added and the cell suspensions are placed in the counting chamber of a BIOLUMINATE (LB 95 05 Berthold Co., Wildbad, FRG). 50 ml of luminol (100 mg/ml) and 100 ml of a stimulus (50 mg/ml zymosan or 100 mg/ml of an immune complex or, to the control, 100 ml of PBS) are added to the contents of the tube, and the light emission is measured (Apple II computer with MX-82 FIT Epson dot matrix printer). To determine the inhibition of MAb, 100 ml of a solution of the MAb is added and the mixture is incubated for 15 minutes (final concentration 100 mg/ml).

The MAbs 494/32, 494/36, 227/18, 431/31 and the others described in German OffenlegunLgsschrift 33 29 184, 227/12 (AK 12) and 227/19 (AK 16) were used, by way of example, in this or the following assay systems, and their binding to the corresponding tumor cell lines were measured in the indirect immunofluorcscence assay of Terasaki (Cancer detection and prevention (1983), 6, 181).

Table 2, which follows, shows the results.

TABLE 2

| | Inhibition of chemiluminescence (%) | | | |
|---|---|---|---|---|
| MAb | Binding assay (Terasaki) | PBS (control) | Stimulus Zymosan | Immune complex |
| 227/12 | negative | 0 | 7 | 3 |
| 431/31 | negative | 0 | 8 | 0 |
| 494/32 | positive | 6 | 59 | 37 |
| 227/18 | positive | 21 | 54 | 66 |
| 227/19 | positive | 17 | 42 | 48 |

It is evident from the table that the MAbs which do not bind to the tumor cell membrane do not inhibit the chemiluminescence whereas those which bind do inhibit it.

This also applies to other MAbs which are suitable as therapeutic agents for tumors.

The procedure for testing the ability of a MAb to inhibit pinocytosis and enzyme secretion was as follows:

$3 \times 10^6$ tumor cells which have been obtained as described above and cultured in 3.5 cm Petri dishes are incubated for 24 hours with the stimuli (zymosan or an immune complex or PBS (control) and, where appropriate, together with 10 mg of MAb per ml), and the ability of the MAbs to inhibit the release of enzymes by the cells is tested as stated in the citations given Bi-glucuronidase, J. Biol. Chem. (1946) 166, 757; Bi-galactosidase: Biochem. J. (1959) 71, 318; lactate dehydrogenase: Methoden der enzymatischen Analyse (Methods of enzyme analysis) Verlag Chemie, Weinheim/Bergstrasse, Federal Republic of Germany, page 533 (1970); Pinocytosis activity: Biochem. Biophys. Res. Comm. (1973) 52, 627).

Table 3 likewise shows that MAbs which bind to the PANC-1 cell also inhibit its enzyme release, whereas others do not cause this.

TABLE 3

| MAb | Enzyme release (% inhibition) | | |
|---|---|---|---|
| | PBS | Zym | IC |
| 494/32 | 21 | 42 | 34 |
| 495/36 | 26 | 86 | 90 |
| 227/18 | 2 | 52 | 52 |
| 227/19 | 0 | 54 | 51 |
| 431/31 | 4 | 7 | 3 |
| 227/12 | 5 | 0 | 0 |

Table 4 shows the ability of monoclonal antibodies to inhibit the basal pinocytosis activity of pancreatic tumor cells after binding to the tumor cell membrane. Those which do not bind do not inhibit the pinocytosis of $^{198}$Au. The results obtained with the F(ab')$_2$ fragment of MAb 494/32 were identical to those with the intact immunoglobulin.

TABLE 4

| MAb | Inhibition of uptake of $^{198}$Au (%) |
|---|---|
| 494/32 | 42 |
| 495/36 | 53 |
| 227/18 | 61 |
| 227/19 | 60 |
| 431/31 | 5 |
| 227/12 | 4 |

Mabs or their non-FC fraagments or other ligands which are able to inhibit all or some of the pancreatic carcinoma cell functions indicated above can be used for the therapy of tumors, in particular of pancreatic carcinomas.

Clinical data after i.v. administration of MAb 494/32 (5× at intervals of one day to a total dose of 210 mg) show that, with progressive pancreatic carcinoma, this MAb causes, after palliative operation, arrest of the disease in 4 of 6 cases (confirmed by computerized tomography) and brings about a subjective improvement in the general condition of the patients. A pharmaceutical suitable for the therapy of tumors contains a MAb or ligand having the properties described in the form of a solution, or in frozen or dried form. One daily dose is in the range 20 to 500 mg per 70 kg of bodyweight. The agent is administered parenterally, preferably infused. An effective amount is administered to the patient in a period of from 1 minute to 3 h. The agent is given in time intervals of from one day up to several months.

The examples which follow illustrate the invention.

EXAMPLE 1

The carcinoma cell line BW X was cultivated in a cell cultured in plastic bottles, growing as a monolayer in RPMI-1640 medium (Moore, G. E., Gerner, R. E., Franklin, H. A., Culture of normal human leukocytes, J.A.M.A. 199, 519–524 (1967)) with 10% fetal calf serum. The adherent cells growing in confluent cultures were separated mechanically or using trypsin which was dissolved in RPMI-1640 medium containing no fetal calf serum, the collagenase was inactivated by addition of fetal calf serum dissolved in RPMI-1640, and then the cells were detached from the tissue culture bottles and washed 3 times in phosphate-buffered saline (PBS) at 37° C.

About $10^7$ cell, the major part of which is in the form of aggregates, were incubated at 37° C. for 1 hour in 1 ml of PBS which contained 100 mg of mitomycin C. Then the cells thus inactivated were washed 3 times with PBS and a) washed 3 times in 0.18 molar ammonium bicarbonate buffer which had been adjusted to pH 7.4 with acetic acid. A cell sediment corresponding to $10^7$ cells was taken up in 100 mi of the same ammonium bicarbonate buffer and frozen at −70° C. The frozen material was then freeze-dried and stored in a small glass bottle, which was closed air-tight, in a refrigerator at +4° C. The cell material thus treated can, after having been taken up in PBS, be used for vaccination of patients. Alternatively, the inactive cells are:

b) incubated with 0.1% glutaraldehyde in PBS at +4° C. for 5 minutes, the excess glutaraldehyde being removed by washing 3 times with PBS, and then incubated with 2% BSA (Bovine Serum Albumin) at +4° C. for 5 minutes and washed 3 times in PBS. The cells thus treated can be stored at +3 ° C. and used for the vaccination of patients, or;

c) incubated in formalin according to Lilly (Benno Romeis (1968), page 65, section 266, Oldenburg Verlag, Munich) at 25° C. overnight, shaking occasionally. The cells (about $10^8$) were centrifuged with decantation of the supernatant (10 minutes at 800×g), and the cell sediment was suspended in 7 ml of double-distilled water (=1st wash). This washing process was repeated 4 times at intervals of 1 hour. The cell sediment was then washed 3 times, at intervals of 1 hour, in 7 ml of 70% ethanol each time. The cell sediment was then washed 3 times, at intervals of 30 minutes, in 7 ml of 70% ethanol each time. The cell sediment was then washed 3 times at intervals of 30 minutes, in 7 ml of 96% ethanol each time. The cell sediment was the washed 3 times, at intervals of 30 minutes, in 7 ml of 99% ethanol each time. The cell sediment was then washed 3 times, at intervals of 30 minutes, in 7 ml of sterile PBS each time, and was stored sterile at 4° C. The cells thus treated can be stored at 4° C. and used for the vaccination of patients.

EXAMPLE 2

In order to isolate antigens from tumor cells by immuno adsorption chromatography, purified monoclonal antibodies which unambiguously react with antigens on the tumor cells which are to be used as a vaccine are covalently bound to CNBr-activated sepharose 4B. The process was that of the Pharmacia book "Affinity Chromatography," Principles and Methods, 12–18 (1979), in particular page 15. The carrier-bound monoclonal antibodies were then incubated with cell solubilizates at +4° C. for 2 hours, shaking occasionally. The latter were obtained from cultured cells, which had been mechanically removed from the culture bottles, by means of extraction with lysis buffer (5 g/l sodium deoxycholate, 0.5 mmol/l PMSF=phenylmethylsulfonyl fluoride, PBS, ph 8.3), as described in Hybridoma 1, 413–421 (1982), in particular on page 414.

The loaded carrier was centrifuged and suspended in lysis buffer-SDS (20 mM tris.HCl ph 8.0, 1 mmol/l PMSF, 5 g/l NONIDET P-40 (=octylphenyl ethylene oxide; Fluka AG), 5 g/l sodium deoxycholate, 1 mmol/l ethylenediaminetetraacetate and 1 g/l sodium dodecyl sulfate SDS)) for washing.

This washing process was repeated 3 times. The carrier was then washed twice in lysis buffer without the addition of SDS and then washed once in a washing buffer (2 M tris. HCl, ph 8.0, 10 mmol/l MaCl, 0.1 mmol/l EDTA and 0.5 g/l NP-40). The antigens thus purified were removed from the solid carrier either by heating at +95° C. for 5 minutes or by incubation in 6 mol/l $NH_4SCN$ at +4° C. for 30 minutes.

What is claimed is:

1. Monoclonal antibodies selected from the group consisting of 250/183-DSM ACC2412, 431/26-DSM ACC2414, 494/32-DSM ACC 2410, and 495/36-DSM ACC2415.

2. The hybridomas which produce the monoclonal antibodies of claim 1.

3. The monoclonal antibody having amino acids encoded by the cDNA sequences for the variable regions set forth in FIG. 4.

4. The monoclonal antibody 494/32-DSM ACC 2410.

5. The monoclonal antibody 250/183-DSM ACC 2412.

6. The monoclonal antibody having amino acids encoded by the cDNA sequences for the variable regions set forth in FIG. 2.

7. The monoclonal antibody 431/26-DSM ACC 2414.

8. The monoclonal antibody having amino acids encoded by the cDNA sequences for the variable regions set forth in FIG. 3.

9. The monoclonal antibody 495/36-DSM ACC 2415.

10. An isolated antibody or antigen-binding fragment thereof having a binding affinity for a tumor-associated antigen, wherein the antibody binds to the same epitope as monoclonal antibody 494/32-DSM ACC 2410, monoclonal antibody 431/26-DSM ACC2414, or monoclonal antibody 495/36-DSM ACC 2415.

11. An in vitro diagnostic aid comprising the monoclonal antibody as claimed in claims 4, 5, 7, or 9 wherein the antibody is immunoreactive with an antigen associated with tumors selected from carcinomas of the breast, ovaries, stomach, pancreas, colon and lung.

12. A diagnostic aid for detecting tumor-associated antigen in biological samples comprising the monoclonal antibody as claimed in claims 3, 5, 7, or 9 wherein the modified antibody is immunoreactive with an antigen associated with tumors selected from carcinomas of the breast, ovaries, stomach, pancreas, colon and lung.

13. A method of post-operatively treating a patient suffering from pancreatic cancer comprising administering parenterally or by infusion to said patient an effective amount of the monoclonal antibody of claims 3 or 4, wherein the monoclonal antibody is administered in a daily dose of 20 to 500 mg per 70 kg of bodyweight.

14. A method of detecting in vitro a tumor-associated antigen derived from a carcinoma of the breast, ovaries, colon, pancreas or lung by binding the monoclonal antibody 494/32-DSM ACC 2410, or fragment thereof, or monoclonal antibody 495/36-DSM ACC 2415, or fragment thereof, to said antigen, and measuring the amount of said binding.

15. The method of claim 14 wherein the antigen is derived from carcinoma of the pancreas.

16. The method according to claim 14 wherein the amount of binding is measured by indirect immunofluorescence assay, inhibition of enzyme release, or inhibition of pinocytosis of colloidal gold.

17. A method of detecting tumors in vivo by radiolabeling the monoclonal antibody as claimed in claims 4 or 9, injecting said radiolabeled monoclonal antibody into a mammal, and detecting the radiolabel by immunoscintigraphy.

18. The method according to claim 17 wherein said antigens are removed from the solid carrier by heating or by incubation.

19. A method for isolating cell-membrane-associated antigens in a sample comprising:

a) covalently binding a monoclonal antibody selected from the monoclonal antibodies of claim 1 to a solid carrier;

b) incubating said carrier-bound antibodies with solubilizates of tumor cells in order to bind said membrane-associated antigens to the carrier-bound antibodies;

c) centrifuging the solid carrier followed by washing said carrier to purify said antigens; and d) removing said antigens from the solid carrier.

* * * * *